United States Patent
Rapoport et al.

(10) Patent No.: US 9,387,719 B2
(45) Date of Patent: Jul. 12, 2016

(54) COLD-WORKED METAL ARTICLES INCLUDING LUMINESCENT PHOSPHOR PARTICLES, METHODS OF FORMING THE SAME, AND METHODS OF AUTHENTICATING THE SAME

(71) Applicant: Honeywell International Inc., Morristown, NJ (US)

(72) Inventors: William Ross Rapoport, Bridgeport, NJ (US); James Kane, Lawrenceville, NJ (US); Carsten Lau, Hannover (DE)

(73) Assignees: HONEYWELL INTERNATIONAL INC., Morris Plains, NJ (US); THE ROYAL MINT LIMITED, Pontyclun (GB)

( * ) Notice: Subject to any disclaimer, the term of this patent is extended or adjusted under 35 U.S.C. 154(b) by 0 days.

(21) Appl. No.: 14/524,928

(22) Filed: Oct. 27, 2014

(65) Prior Publication Data
US 2015/0115177 A1    Apr. 30, 2015

Related U.S. Application Data

(60) Provisional application No. 61/956,179, filed on Oct. 28, 2013, provisional application No. 61/980,212, filed on Apr. 16, 2014.

(51) Int. Cl.
*G01N 21/64* (2006.01)
*B42D 25/29* (2014.01)
(Continued)

(52) U.S. Cl.
CPC ............... *B42D 25/29* (2014.10); *G01N 21/64* (2013.01); *G01N 21/643* (2013.01); *G07D 5/00* (2013.01);
(Continued)

(58) Field of Classification Search
CPC ....... G07D 7/122; G07D 7/124; G07D 7/205; G01N 2021/8427; B42D 25/29
See application file for complete search history.

(56) References Cited

U.S. PATENT DOCUMENTS 2,804,408 A  *  8/1957 Gregory ..................... 148/684
5,514,479 A     5/1996 Feldstein
(Continued)

FOREIGN PATENT DOCUMENTS

CN         101560679 A    10/2009
CN         101560681 A    10/2009
(Continued)

OTHER PUBLICATIONS

Feldstein, Coatings with Identification Properties, EN 2010 Conference, Nov. 8-9, 2010, Charleston, SC.
(Continued)

*Primary Examiner* — Kiho Kim
(74) *Attorney, Agent, or Firm* — Ingrassia Fisher & Lorenz, P.C.

(57) ABSTRACT

Cold-worked metal articles, methods of forming cold-worked metal articles, and methods of authenticating cold-worked metal articles are provided. In an embodiment, a cold-worked metal article includes a cold-worked metal-containing surface that defines pores. The cold-worked metal-containing surface includes luminescent phosphor particles disposed within the pores. The luminescent phosphor particles include a host crystal lattice material and at least one active ion that includes an absorbing ion and an emitting ion that is different from the absorbing ion. The luminescent phosphor particles are harder than the cold-worked metal-containing surface.

20 Claims, 2 Drawing Sheets

(51) Int. Cl.
  *G09F 5/00* (2006.01)
  *G07D 5/00* (2006.01)
  *G07D 7/12* (2016.01)
  *G07D 7/20* (2016.01)
  *G01N 21/84* (2006.01)

(52) U.S. Cl.
  CPC ............... *G07D 7/122* (2013.01); *G07D 7/124* (2013.01); *G07D 7/205* (2013.01); *G09F 5/00* (2013.01); *G01N 2021/8427* (2013.01); *Y10T 428/12479* (2015.01); *Y10T 428/249921* (2015.04)

(56) References Cited

U.S. PATENT DOCUMENTS

| | | | |
|---|---|---|---|
| 5,516,591 A | | 5/1996 | Feldstein |
| 5,834,065 A | | 11/1998 | Feldstein |
| 6,506,476 B1 | * | 1/2003 | Kaule et al. ................ 428/195.1 |
| 7,622,163 B2 | | 11/2009 | Crawford et al. |
| 8,192,602 B2 | | 6/2012 | Zaban et al. |
| 2006/0068194 A1 | | 3/2006 | Feldstein |
| 2008/0060907 A1 | | 3/2008 | Oka |
| 2008/0152826 A1 | * | 6/2008 | Crawford et al. ............. 427/466 |
| 2008/0197620 A1 | * | 8/2008 | Spencer et al. ................. 283/81 |
| 2009/0258200 A1 | | 10/2009 | Scholz et al. |
| 2010/0084852 A1 | | 4/2010 | Hampden-Smith et al. |
| 2010/0140501 A1 | | 6/2010 | Lawandy |
| 2011/0305919 A1 | | 12/2011 | Conroy et al. |
| 2012/0021120 A1 | | 1/2012 | Feldstein |
| 2012/0187341 A1 | | 7/2012 | Strek |
| 2013/0214523 A1 | | 8/2013 | Kecht et al. |

FOREIGN PATENT DOCUMENTS

| | | |
|---|---|---|
| CN | 101560682 A | 10/2009 |
| JP | 3967796 B2 | 8/2007 |
| WO | 0018591 A1 | 4/2000 |
| WO | 2005000743 A2 | 1/2005 |

OTHER PUBLICATIONS

Feldstein et al., High Speed Electroless Nickel—PTFE Plating, National Association for Surface Finishing, Indiana Convention Center, Jun. 16-18, 2008.

The Written Opinion and International Search Report mailed Feb. 4, 2015 in International Application No. PCT/US2014062518.

* cited by examiner

COLD-WORKED METAL ARTICLES INCLUDING LUMINESCENT PHOSPHOR PARTICLES, METHODS OF FORMING THE SAME, AND METHODS OF AUTHENTICATING THE SAME

PRIORITY CLAIMS

This application claims the benefit of U.S. Provisional Application No. 61/956,179, filed Oct. 28, 2013, and U.S. Provisional Application No. 61/980,212, filed Apr. 16, 2014.

TECHNICAL FIELD

The technical field generally relates to cold-worked metal articles that include an authentication feature, and methods of forming and authenticating the cold-worked metal articles. More particularly, the invention relates to cold-worked metal articles that include luminescent phosphor particles, and methods of forming and authenticating the cold-worked metal articles that include the luminescent phosphor particles.

BACKGROUND

In many applications, it is necessary to distinguish an original article from a copy or counterfeit to validate the original article. An original article that includes an authenticating feature can be validated in many ways. Some methods involve visible (i.e. overt) authenticating features that are disposed on or incorporated into the article, such as a hologram on a credit card, an embossed image or watermark on a bank note, a security foil, a security ribbon, colored threads or colored fibers within a bank note, or a floating and/or sinking image on a passport. While these features are easy to detect with the eye and may not require equipment for authentication, these overt features are easily identified by a would-be forger and/or counterfeiter. As such, in addition to overt features, hidden (i.e. covert) features may be incorporated in original articles. Examples of covert features include invisible fluorescent fibers, chemically sensitive stains, and taggants such as luminescent pigments or fluorescent dyes that are incorporated into the substrate of the article. Covert features may also include physical properties of the original articles to be validated. For example, for metal articles such as coins, authentication may be determined through conductivity measurements. However, due to cost considerations, many coins are now produced with a soft steel core plated with another metal, such as nickel. The soft steel core generally produces a magnetic signal that masks any magnetic signal from the plated metal and, thus, renders authentication through conventional conductivity measurements difficult.

It is generally known to provide taggants on a surface of metal articles to enable authentication of the metal articles. Existing efforts to employ taggants in metal articles of manufacture involve post metal-forming surface deposition of taggants because taggant costs are prohibitive to dispersing the taggants through the entire material volume when only the surface is subject to authentication. Further, article manufacturing techniques may have an unpredictable effect on taggant properties such that post metal-forming surface deposition of the taggants is the only option. However, post metal-forming surface deposition of the taggants results in weakly adhered taggants that easily wear off. Wear is not a concern when determining if a new product is real or counterfeit when purchased from a supplier because authentication is a one-time event. However, repeat authentication over time is a concern for value articles, such as coins, that are subject to significant wear.

Accordingly, it is desirable to provide metal articles and methods of forming metal articles that include taggants that are robustly adhered to the metal articles. Further, there remains an opportunity for methods of authenticating metal articles with the taggants that are robustly adhered to the metal articles. Furthermore, other desirable features and characteristics of the present invention will become apparent from the subsequent detailed description of the invention and the appended claims, taken in conjunction with the accompanying drawings and this background of the invention.

BRIEF SUMMARY

Cold-worked metal articles, methods of forming cold-worked metal articles, and methods of authenticating cold-worked metal articles are provided. In an embodiment, a cold-worked metal article includes a cold-worked metal-containing surface that includes pores. The cold-worked metal-containing surface includes luminescent phosphor particles disposed within the pores. The luminescent phosphor particles include a host crystal lattice material and at least one active ion that includes an absorbing ion and an emitting ion that is different from the absorbing ion. The luminescent phosphor particles are harder than the cold-worked metal-containing surface.

In another embodiment, a method of forming a cold-worked metal article includes providing a metal substrate having a surface. A coating is formed on the surface of the metal substrate to produce an intermediate article. The coating includes luminescent phosphor particles. The luminescent phosphor particles include a host crystal lattice material and at least one active ion that includes an absorbing ion and an emitting ion that is different from the absorbing ion. The intermediate article is cold-worked to produce the cold-worked metal article.

In another embodiment, a method of authenticating a cold-worked metal article includes providing the cold-worked metal article that includes a cold-worked metal-containing surface that includes pores. Luminescent phosphor particles are disposed within the pores and the luminescent phosphor particles include a host crystal lattice material and at least one active ion that includes an absorbing ion and an emitting ion that is different from the absorbing ion. The luminescent phosphor particles are harder than the cold-worked metal-containing surface. The cold-worked metal article is exposed to light produced by an exciting light source. The exciting light source produces light having sufficient intensity to excite the luminescent phosphor particles. The presence of the luminescent phosphor particles is detected in the cold-worked metal article with a detector.

BRIEF DESCRIPTION OF THE DRAWINGS

The various embodiments will hereinafter be described in conjunction with the following drawing figures, wherein like numerals denote like elements, and wherein.

DETAILED DESCRIPTION

Figure 1:
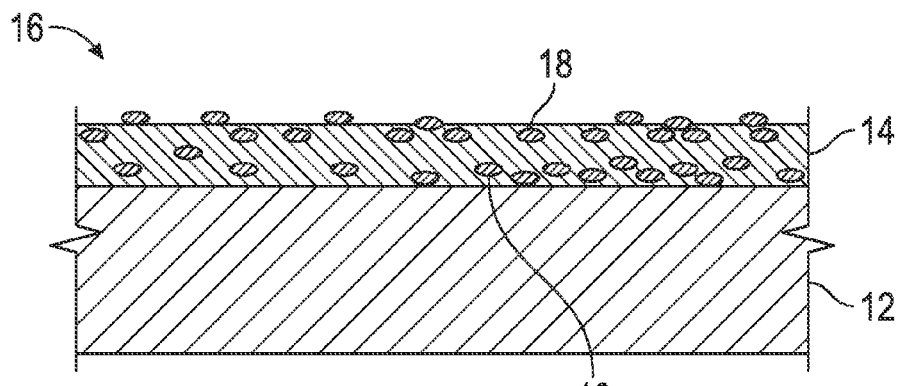
FIG. 1 is a schematic cross-sectional side view of an intermediate article including a metal substrate and a composite coating formed thereon that includes luminescent phosphor particles prior to cold-working in accordance with an embodiment.

The following detailed description is merely exemplary in nature and is not intended to limit the various embodiments or the application and uses thereof. Furthermore, there is no intention to be bound by any theory presented in the preceding background or the following detailed description.

Cold-worked metal articles, methods of forming the cold-worked metal articles, and methods of authenticating the cold-worked metal articles are provided herein. "Cold-worked," as referred to herein, means that the metal article is formed through a cold-working or cold-forming technique that involves application of elevated pressure under temperatures below a recrystallization temperature to effectuate plastic deformation of the metal articles, i.e., a permanent deformation of the metal articles without fracture under the action of a sustained force. Examples of cold-working techniques include striking, embossing, molding, rolling, and the like. The cold-worked metal articles have a cold-worked metal-containing surface that includes pores, with luminescent phosphor particles disposed within the pores. "Metal-containing surface," as referred to herein, refers to material at the surface of the metal article that contains metal or metal-containing compounds and into which the luminescent phosphor particles are embedded after cold-forming. In various embodiments, the cold-worked metal-containing surface may be a surface of an uncoated metal substrate, or may be a surface of a coating that is disposed on a metal substrate (e.g., a plated coating). The luminescent phosphor particles are harder than the cold-worked metal-containing surface such that the material of the cold-worked metal-containing surface yields before the luminescent phosphor particles during cold-working. As a result, during cold-working, the luminescent phosphor particles that are at or near the metal-containing surface are forced under pressure into the cold-worked metal-containing surface and form the pores, or holes, in the cold-worked metal-containing surface, with the luminescent phosphor particle remaining disposed in the pore and with at least some of the luminescent phosphor particles being at least partially uncovered by the material of the cold-worked metal-containing surface. In particular, during cold-working, the pressure is generally of such a high magnitude that the material of the metal-containing surface may partially reflow over the luminescent phosphor particles in the pores provided that at least some of the luminescent phosphor particles are not completely covered by the material of the cold-worked metal-containing surface. In other embodiments, the metal-containing surface may completely reflow over the luminescent phosphor particles in the pores, with subsequent surface removal conducted to remove some of the metal-containing surface to again expose the luminescent phosphor particles in the pores. In this regard, dimensions of the pores are custom to the individual particles that are disposed in the pores. With the luminescent phosphor particles depressed into the cold-worked metal-containing surface after cold-working, the luminescent phosphor particles are more robustly adhered to the cold-worked metal articles than particles that are adhered after cold-working. Further, because the luminescent phosphor particles are harder than the cold-worked metal-containing surface, the metal-containing surface deforms under pressure during cold-working and the luminescent phosphor particles remain intact.

An embodiment of a cold-worked metal article and a method of forming the cold-worked metal article will now be described with reference to FIGS. 1 and 2. In this embodiment and as shown in FIG. 1, a metal substrate 12 is provided. The metal substrate 12 includes metal-containing material, and the types of metal-containing material that are suitable for the metal substrate 12 are not limited. In embodiments, one or more metals are included in the metal-containing material in a total amount of at least 50 weight %, based on the total weight of the metal-containing material. Examples of suitable metals that may be employed include, but are not limited to, tin, copper, iron, aluminum, zinc, nickel, gold, silver, brass, platinum, and combinations thereof. The metal-containing material may be an alloy of one or more metals along with other non-metal elements. In embodiments, the cold-worked metal articles are employed as coins, in which case the metal substrate 12 may be a conventional material that is employed as a core of coins such as soft steel or zinc.

In an embodiment and as also shown in FIG. 1, a coating 14 is formed on a surface of the metal substrate 12 to produce an intermediate article 16 prior to subsequent cold-working as described in further detail below. The coating 14 includes luminescent phosphor particles 18 and, optionally, other components that may be employed to adhere the luminescent phosphor particles 18 to the metal substrate 12, or to provide finishing features to the resulting cold-worked metal article. The coating 14 may be formed continuously or sporadically on the surface of the metal substrate 12. In various embodiments, the coating 14 may be formed over the surface of the entire metal substrate 12, or alternatively may be formed only in localized areas of the metal substrate 12. Further, the coating 14 may be formed on planar surfaces of the metal substrate 12 or on edges thereof, depending upon desired locations for the luminescent phosphor particles 18 in the cold-worked metal articles. In this regard, the coating 14 may be provided primarily for placing luminescent phosphor particles 18 on the surface of the metal substrate 12, or the coating 14 may be provided as a show surface, such as a plating on the metal substrate 12. The coating 14 may be formed through various deposition techniques that are not particularly limited. For example, the coating 14 may be formed through pad printing, stamping, plating, spraying, and the like. In an embodiment and as shown in FIG. 1, the coating 14 is a composite coating 14 that includes a metal-containing material with the luminescent phosphor particles 18 dispersed in the metal-containing material. The "metal-containing material," as referred to herein, is a material that contains one or more metals, that is suitable as a surface coating, and that may be formed on the metal substrate 12 through conventional surface coating techniques. The metal-containing material provides a continuous phase in the composite coating 14, with the luminescent phosphor particles 18 interspersed within the continuous phase. In an embodiment the metal-containing material is a material that can be deposited on the metal substrate 12 through plating techniques, although other surface coating techniques such as sputtering, dipping, spraying, and the like are also possible in accordance with the methods described herein. Suitable metals for the metal-containing matrix may be any of those described above for the metal substrate 12. Specific examples of suitable materials for the metal-containing matrix include nickel, copper, and brass.

The luminescent phosphor particles 18 are dispersed within the metal-containing material, which avoids unnecessary inclusion of luminescent phosphor particles 18 through the entire bulk of the resulting cold-worked metal article while providing the luminescent phosphor particles 18 to a desired depth in the resulting cold-worked metal article and at the surface thereof, where the luminescent phosphor particles 18 can be detected by exposing the cold-worked metal article to light produced by an exciting light source, as described in further detail below. The composite coating 14 may be formed with a thickness prior to cold-working of at least about 10 microns, such as from about 10 to about 50 microns, or such as from about 10 to about 25 microns with the luminescent phosphor particles 18 dispersed throughout the composite coating 14. Such thicknesses of the composite coating 14 enable the cold-worked metal article to be authenticated over time and even under conditions where the composite coating 14 may be subject to significant wear, such as under circumstances where the cold-worked metal article is a coin or token. In particular, with the luminescent phosphor particles 18 being dispersed throughout the composite coating 14, some luminescent phosphor particles 18 remain buried within the composite coating 14 after cold-working. Erosion of the composite coating 14 results in exposure of previously-buried luminescent phosphor particles 18, thereby allowing the exposed luminescent phosphor particles 18 to be excited during authentication.

To provide for substantially uniform dispersal of the luminescent phosphor particles 18 within the metal-containing material, the luminescent phosphor particles 18 may have a sufficiently small average particle size to resist settling and maintain suspended within the metal-containing material prior to and after forming the composite coating 14 on the metal substrate 12. Further, it is desirable to create a visually appealing surface of the cold-worked metal article that is very similar to one that has no luminescent phosphor particles 18 such that upon even somewhat close inspection, the article appears to be authentic, and relatively small particle sizes enable such appearance to be achieved. In an embodiment, the luminescent phosphor particles 18 have an average nominal particle diameter with an particle size distribution (D50) of less than or equal to about 2 microns, such as less than about 1.6 microns, or such as from about 0.5 to about 1.6 microns to enable a stable dispersion of the luminescent phosphor particles 18 in the metal-containing material to be attained. Optionally, a dispersant may be included in the composite coating 14 to assist with dispersing the luminescent phosphor particles 18 in the metal-containing material.

Because the intermediate article 16 is cold-worked after forming the coating 14 on the metal substrate 12, the luminescent phosphor particles 18 are harder than a cold-worked metal-containing surface of the resulting cold-worked metal article to enable the luminescent phosphor particles 18 to resist pulverization during cold-working. In the embodiment shown in FIG. 1, the surface of the resulting cold-worked metal article is a surface of the composite coating 14, and the luminescent phosphor particles 18 are harder than the metal-containing material of the composite coating 14. The Mohs scale is commonly used and compares the hardness of various materials on a 1-10 ordinal scale. Due to the large difference in metallic hardness, a wide range of mineral-like particles are substantially harder and are potential candidates for incorporation. Examples of hardness values for various metals, on the Mohs scale, are: gold 2.5, silver 2.5, copper 2.5-3, iron 4, nickel 4, steel 4-4.5, platinum 4-4.5. As such, in embodiments, the luminescent phosphor particles 18 have a Mohs hardness of greater than 4.5, such as at least 6, or such as from about 6.5 to about 9.5 Further, because the luminescent phosphor particles 18 are disposed in pores in the cold-worked metal-containing surface of the resulting cold-worked metal article and because material on the surface of the resulting cold-worked metal article may partially reflow over the luminescent phosphor particles 18 in the pores with only a portion of the luminescent phosphor particles 18 exposed, suitable luminescent phosphor particles 18 may include those that provide a sufficiently strong absorption and emission to enable detection upon exposure to light from an exciting light source. Strong absorption provides advantages since more rare earth based luminescent phosphors are weak in absorption, resulting in an insufficient number of visible or IR emitting transitions that are capable of being detected. Luminescent phosphor particles 18 that provide the sufficiently strong absorption and emission also enable phosphor loading to be minimized, thereby preserving physical properties and appearance of the metal-containing material that is achieved in the absence of the luminescent phosphor materials. For example, in embodiments the luminescent phosphor particles 18 may be present in the composite coating 14 in an amount of at least about 0.05 weight %, such as from about 0.1 to about 2 weight %, or such as from about 0.05 to about 1 weight %, based on the total weight of the composite coating 14. The amount of the luminescent phosphor particles 18 that is also generally correlated to the size of the particles.

The luminescent phosphor particles 18 function by absorbing light or radiation from an exciting light source and then emitting radiation at particular wavelengths based upon chemistry of the luminescent phosphor particles 18. In embodiments, suitable luminescent phosphor particles 18 exhibit high absorption of light or radiation from the exciting light source, high quantum efficiency, and ultimately emission at a high peak signal level. For example, in embodiments, suitable luminescent phosphor particles 18 emit in the infrared spectrum (i.e., at wavelengths of greater than about 700 nm) and exhibit broad absorption bands in either the visible and/or infrared spectra. As another example, in other embodiments, suitable luminescent phosphor particles 18 have an emission at a wavelength of less than or equal to about 1100 nm, such as from about 700 nm to about 1100 nm, and an emission at a wavelength of greater than about 1100 nm Suitable luminescent phosphor particles 18 include a host crystal lattice material and at least one active ion that includes an absorbing ion and an emitting ion that is different from the absorbing ion. The host crystal lattice material includes a material into which the active ions are incorporated (e.g., substituted). As used herein, the term "substituted" means substituted at any percentage, including low, medium, and high substitution percentages. The host crystal lattice material may be in the form of a crystal lattice into which different chemical constituents may substitute various positions within the crystal lattice. As used herein, the term "active ion" refers to an ion in the luminescent phosphor particles 18 that may absorb, transfer, and/or emit energy. The amount of each ion substituted into the host crystal lattice material is generally described in terms of atomic percent, where the total number of ions of the host crystal lattice material that may be theoretically replaced by active ions is equal to 100%, which value does not include ions of the host crystal lattice material that cannot be replaced. An ion of the host crystal lattice material that allows for replacement with active ions may have similar size, the same valance state or similar loading, and similar coordination preference as the ions with which it will be replaced. As various substitutable positions within a host crystal lattice material may occur, the ions on each of these positions will be accounted for 100 atomic percent.

Examples of suitable host crystal lattice materials include oxide-containing material such as those chosen from an aluminate, a borate, a gallate, a niobate, vanadate, a garnet, a pervoskite, an oxysulfide, and combinations thereof. Specific examples of suitable garnet host crystal lattice materials include, but are not limited to, those chosen from yttrium aluminum garnet (YAG), yttrium gallium garnet (YGG), yttrium iron garnet (YIG), or gadolinium gallium garnet (GGG), gadolinium scandium gallium garnet (GSGG), and mixtures thereof, which are all both chemically stable and possess the desired hardness to resist pulverizing during cold-working into metal-containing material that possesses a lower Mhos hardness. The aforementioned specific examples of host crystal lattice material are also capable be being milled to low average particle diameters within the ranges set forth above.

It is to be appreciated that the luminescent phosphor particles 18 may include a combination of active ions, depending upon a particular mechanism by which the luminescent phosphor particles 18 absorb and emit radiation. As alluded to above, the at least one active ion includes an absorbing ion and an emitting ion that is different from the absorbing ion, and can include a combination of different emitting ions and absorbing ions. The luminescent phosphor particles 18 produce radiation by absorption of incident radiation by either or both of the host crystal lattice material and the absorbing ion(s), energy transfer from the host crystal lattice material/absorbing ion(s) to the emitting ion(s), and radiation of the transferred energy by the emitting ion(s). In whichever manner the exciting radiation is absorbed, the emitting ion(s) of the luminescent phosphor particles 18 produces emitted radiation having a unique spectral signature and a measurable decay time constant (Tau).

Absorbing ions and emitting ions may be chosen that exhibit high absorption of light or radiation from the exciting light source, high quantum efficiency, and ultimately emission at a high peak signal level to enable detection when the luminescent phosphor particles 18 are disposed in the pores. For example, in embodiments, suitable absorbing ions may be chosen from chromium, iron, erbium, neodymium, ytterbium, or combinations thereof, with the absorbing ion substituted into the host crystal lattice material. Chromium and iron are particularly effective as primary absorbers, which then transfer absorbed energy over to rare earth ions. The absorbing ions may be substituted in an amount of at least about 1 atomic percent, such as from about 10 to about 50 atomic percent, or from about 20 to about 25 atomic percent, based on a total number of ions of the host crystal lattice material that may be theoretically substituted. In the specific case of YIG, iron is incorporated into the host crystal lattice material and is considered part of the host crystal lattice material (and not a separate absorbing ion), with no other absorbing ion necessary for YIG. As such, with YIG, the host crystal lattice material absorbs incident radiation and transfers energy to the emitting ion(s) as described above.

Suitable emitting ions may be chosen from erbium, thulium, ytterbium, holmium, neodymium, and combinations thereof, provided that the emitting ions are different from the absorbing ions. In various embodiments, the total amount of emitting ion(s) substituted into the host crystal lattice material is sufficient to cause the luminescent phosphor particles 18 to produce a detectable emission after being appropriately subjected to exciting radiation. For example, the total amount of emitting ion(s) substituted in the host crystal lattice material may be in a range from about 0.095 atomic percent to about 99.995 atomic percent. However, the amount of emitting ion(s) that may be substituted while still producing the functionality of the luminescent phosphor (e.g., the functionality of producing an emission upon exposure to exciting radiation) depends on the type of ion that is being substituted. In other words, some ions may be substituted at relatively high percentages while still maintaining the functionality of the luminescent phosphor particles 18, but the functionality may be defeated if other ions are substituted at the same, relatively high percentages.

In specific embodiments, examples of suitable luminescent phosphor particles 18 include oxysulfide host crystal lattice material with erbium as an absorbing ion and thulium as an emitting ion; YGG, YAG, and GGG host crystal lattice material with chromium as an absorbing ion and one or more of the following emitting ions: erbium, thulium, or holmium; and YIG host crystal lattice material with no additional absorbing ion and one or more of the following emitting ions: erbium, thulium, or holmium. For various applications, luminescent phosphor particles 18 that emit radiation at a wavelength of less than or equal to about 1100 nm (e.g., with peak emission from about 400 nm to about 1100 nm), are desirable because emissions of less than or equal to about 1100 nm can be detected with silicon detectors, which are relatively cost-effective as compared to other detection equipment. The silicon detectors may be employed in point-of-sale devices, such as vending machines, amusement devices, or change machines, for authentication. Examples of luminescent phosphor particles 18 that emit at less than or equal to about 1100 nm include those that include a garnet as the host crystal lattice material with chromium as the absorbing ion and neodymium or ytterbium as the emitting ions. Specific examples of luminescent phosphor particles 18 that have a peak emission at less than or equal to about 1100 nm include the following: YAG and YGG with chromium as the absorbing ion and ytterbium as the emitting ion.

For various other applications, luminescent phosphor particles 18 that emit radiation at a wavelength of greater than 1100 nm (e.g., with peak emission at greater than 1100 nm) are acceptable and desired because a greater number of combinations of host crystal lattice material and active ions are available that satisfy the other physical properties parameters described herein, thereby enabling a more covert chemical signature to be employed. In yet other embodiments, a combination of luminescent phosphor particles 18 that emit above and below 1100 nm may be employed. The combination of luminescent phosphor particles may be useful under circumstances where a large number of unique signal combinations are desired, with the combination enabling control of a ratio of infrared and UV emissions.

In another specific embodiment, suitable luminescent phosphor particles 18 include a garnet host crystal lattice material, a chromium absorbing ion, a first emitting ion that has an emission at a wavelength of less than or equal to about 1100 nm, and a second emitting ion that has an emission at a wavelength of greater than about 1100 nm. In this embodiment, the luminescent phosphor particles provide for emission wavelengths at both less than or equal to about 1100 nm and greater than 1100 nm to thereby eliminate a need to include multiple different luminescent phosphor particles in the cold-worked metal articles. As a result, the cold-worked metal articles exhibit consistent signal levels for emissions at wavelengths of less than or equal to about 1100 nm and emissions at wavelengths of greater than 1100 nm across different cold-worked metal articles. Because the luminescent phosphor particles 18 of this embodiment include both the first emitting ion and the second emitting ion, metal articles that include the luminescent phosphor particles 18 exhibit consistent signal levels for emissions at wavelengths of less than or equal to about 1100 nm and emissions at wavelengths of greater than 1100 nm across different metal articles. Conversely, when multiple different taggants are employed to provide emissions at wavelengths less than or equal to about 1100 nm and emissions at wavelengths above 1100 nm, the multiple different taggants have a tendency to segregate in the coating composition, thereby rendering uniform application of the multiple different taggants on the surface of the metal articles difficult to achieve and resulting in inconsistent signal levels. Inconsistent signal levels associated with systems that include multiple different taggants having the aforementioned emission properties are avoided by employing the luminescent phosphor particles 18 of this embodiment.

Examples of suitable garnet host crystal lattice materials include any garnet into which chromium can be substituted. Specific examples of suitable garnet host crystal lattice materials include, but are not limited to, those chosen from YAG, YGG, GGG, GSGG, and mixtures thereof. The chromium absorbing ion, the first emitting ion, and the second emitting ion are substituted into the garnet host crystal lattice material, and the luminescent phosphor particles 18 produce radiation by absorption of incident radiation by either or both of the host crystal lattice material and the chromium absorbing ion(s), energy transfer from the host crystal lattice material/chromium absorbing ion to the emitting ion(s), and radiation of the transferred energy by the emitting ion(s). In embodiments, all detectable luminescent phosphor particles 18 in the cold-worked metal article have the same first emitting ions and second emitting ions. Due to the presence of the first emitting ion and the second emitting ion in the luminescent phosphor particles 18 of this embodiment, the luminescent phosphor particles 18 have an emission at a wavelength of less than or equal to about 1100 nm and an emission at a wavelength of greater than about 1100 nm, thereby enabling emissions within both wavelength ranges from a single type of luminescent phosphor. Depending upon the type of garnet host crystal lattice, first emitting ion, and second emitting ion, various different kinetic pathways for energy transfer and emission may occur as described in further detail below, with such pathways impacting amounts of the various ions that are required to attain a certain emission.

The first emitting ion and the second emitting ion are different from the chromium absorbing ion. Suitable first emitting ions that have the emission at the wavelength of less than or equal to about 1100 nm may be chosen from ytterbium, neodymium, and combinations thereof. In various embodiments, the total amount of the first emitting ion(s) substituted into the garnet host crystal lattice material is sufficient to cause the luminescent phosphor particles 18 to produce a detectable emission at a wavelength of less than or equal to about 1100 nm after being appropriately subjected to exciting radiation. For example, the total amount of the first emitting ion(s) substituted in the garnet host crystal lattice material may be in a range from about 0.095 atomic percent to about 99.995 atomic percent. However, the amount of first emitting ion(s) that may be substituted while still producing the functionality of the luminescent phosphor particles 18 (e.g., the functionality of producing an emission at a wavelength of less than or equal to about 1100 nm upon exposure to exciting radiation) depends on the type of ion that is being substituted. In other words, some first emitting ions may be substituted at relatively high percentages while still maintaining the functionality of the luminescent phosphor particles 18, but the functionality may be defeated if other first emitting ions are substituted at the same, relatively high percentages.

Suitable second emitting ions that have the emission at the wavelength of greater than about 1100 nm may be chosen from erbium, thulium, holmium, and combinations thereof. In various embodiments, the total amount of the second emitting ion(s) substituted into the garnet host crystal lattice material is sufficient to cause the luminescent phosphor particles 18 to produce a detectable emission at a wavelength of greater than about 1100 nm after being appropriately subjected to exciting radiation. For example, the total amount of the second emitting ion(s) substituted in the garnet host crystal lattice material may be in a range from about 0.1 atomic percent to about 6 atomic percent. However, the amount of second emitting ion(s) that may be substituted while still producing the functionality of the luminescent phosphor particles 18 (e.g., the functionality of producing an emission at a wavelength of greater than about 1100 nm upon exposure to exciting radiation) depends on the type of ion that is being substituted and the type of garnet host crystal lattice material used. In other words, some second emitting ions may be substituted at relatively low percentages while still maintaining the functionality of the luminescent phosphor particles 18, but the functionality may be defeated if other second emitting ions are substituted at the same, relatively low percentages, or if different garnet host crystal lattice materials are employed.

One specific example of a suitable luminescent phosphor particle 18 includes YAG host crystal lattice material with the chromium absorbing ion, ytterbium as the first emitting ion, and erbium as the second emitting ion. In this embodiment, the chromium absorbing ion may be substituted in an amount of at least about 1 atomic percent, such as from about 10 to about 50 atomic percent, or from about 20 to about 25 atomic percent, based on a total number of ions of the garnet host crystal lattice material that may be theoretically substituted. The erbium is substituted in the garnet host crystal lattice material in an amount of from about 0.1 to about 0.5 atomic percent, based on a total number of ions of the garnet host crystal lattice material that may be theoretically substituted. Such relatively low amounts of the erbium are effective to produce the desired emission at the wavelength of greater than about 1100 nm because the kinetic pathway for energy transfer favors energy transfer from chromium to ytterbium, then to erbium. Another specific example of a suitable luminescent phosphor particle 18 includes YGG host crystal lattice material with the chromium absorbing ion, ytterbium as the first emitting ion, and erbium as the second emitting ion. In this embodiment, the chromium absorbing ion is substituted in the garnet host crystal lattice material in the same amounts as set forth above, and the erbium is substituted in the garnet host crystal lattice material in an amount of from about 1 to about 3 atomic percent, based on a total number of ions of the garnet host crystal lattice material that may be theoretically substituted. Such relatively higher amounts of the erbium are desired to produce the desired emission at the wavelength of greater than about 1100 nm because the kinetic pathway for energy transfer favors energy transfer directly from chromium to erbium.

As set forth above, the luminescent phosphor particles 18 of this embodiment emit radiation at a wavelength of less than or equal to about 1100 nm (e.g., with peak emission from about 400 nm to about 1100 nm) and at a wavelength of greater than about 1100 nm. Such luminescent phosphor particles 18 are desirable because emissions of less than or equal to about 1100 nm can be detected with silicon detectors, which are relatively cost-effective as compared to other detection equipment. The silicon detectors may be employed in point-of-sale devices, such as vending machines, amusement devices, or change machines, for authentication. At the same time, the luminescent phosphor particles 18 of this embodiment are also suitable for various other applications where emissions from the luminescent phosphor particles 18 are desirable at a wavelength of greater than 1100 nm (e.g., with peak emission at greater than 1100 nm) because a greater number of combinations of host crystal lattice material and active ions are available that satisfy the other physical properties parameters described herein, thereby enabling a more covert chemical signature to be employed. The combination of emissions at wavelengths of less than or equal to about 1100 nm and greater than about 1100 nm enables a large number of unique signal combinations to be achieved by varying relative amounts of the chromium absorbing ion, the first emitting ion, and the second emitting ion, as well as by varying the type of garnet host crystal lattice material, first emitting ion, and second emitting ion with the various combinations enabling control of a ratio of infrared and UV emissions.

Figure 2A:
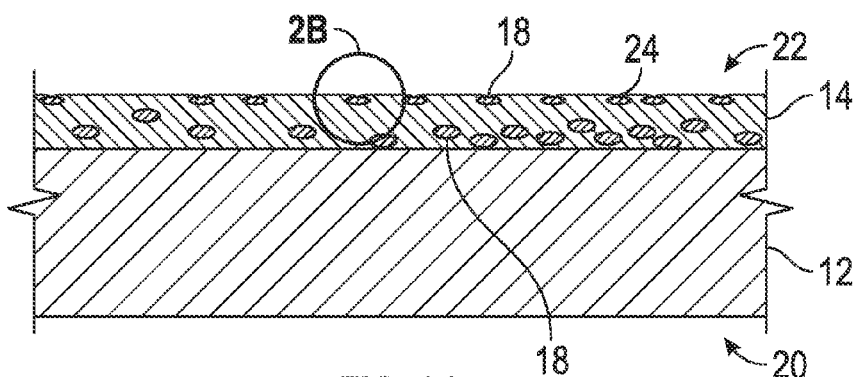
FIG. 2A is a schematic cross-sectional side view of a cold-worked metal article formed from the intermediate article of FIG. 1 after cold-working.
Figure 2B:
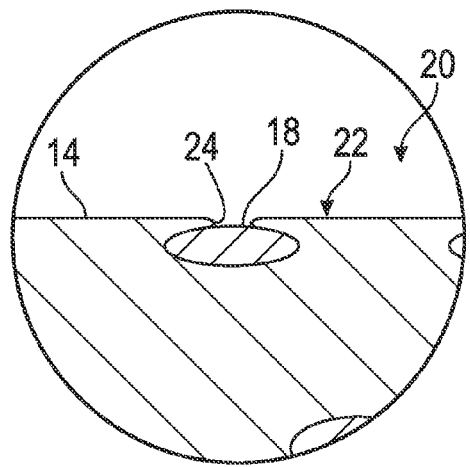
FIG. 2B is a magnified view of a portion of the cold-worked metal article of FIG. 2A.

After forming the coating 14 on the metal substrate 12, the intermediate article 16 is cold-worked to produce the cold-worked metal article 20, as shown in FIGS. 2A and 2B. Although various techniques for cold-working are suitable, in an embodiment, the intermediate article is cold-worked by striking the intermediate article with a die to form the cold-worked metal article 20. Striking with a die may be appropriate during coin fabrication, as well as in other applications where authentication may be desired. The resulting cold-worked metal article 20 includes a cold-worked metal-containing surface 22 that includes pores 24 with luminescent phosphor particles 18 disposed in the pores 24. In this embodiment, the composite coating 14 is present on the metal substrate 12 during cold-working and the cold-worked metal-containing surface 22 is a surface of the composite coating 14 after cold-working. Surface appearance properties and presence of the luminescent phosphor on the cold-worked metal-containing surface 22 of the cold-worked metal article 20 are a concern. Because the luminescent phosphor particles 18 are harder than the metal-containing material in this embodiment, the luminescent phosphor particles 18 near the surface of the composite coating 14 prior to cold-working are depressed into the composite coating 14 during cold-working and are responsible for forming the pores 24. As shown in FIG. 2B, the metal-containing material of the composite coating 14 may partially reflow over the luminescent phosphor particles 18 in the pores 24. In embodiments, the pores 24 have a diameter at an open aperture thereof of at least 0.1 micron to enable the luminescent phosphor particles 18 to be reached by incident radiation. Generally, the diameter at the open aperture of the pores 24 is smaller than the diameter of the luminescent phosphor particles 18. For example, the diameter at the open aperture of the pore 24 may be about 10% of the diameter of the luminescent phosphor particles 18 and the relative ratios of diameter at the open aperture 24 to the diameter of the luminescent phosphor particles 18 shown in the Figures is not to be viewed as representative of actual relative ratios. Because the luminescent phosphor particles 18 have such small dimensions and are generally present in minor amounts as described above, surface appearance is generally visibly unchanged as compared to cold-worked metal articles that do not include the luminescent phosphor particles.

The cold-worked metal-containing surface 22 that includes the pores 24 generally has a higher concentration of luminescent phosphor particles 18 (e.g., down to a depth of from about 1 to 5 microns) than underlying regions thereof because luminescent phosphor particles 18 are pushed down and accumulate at the cold-worked metal-containing surface 22 after cold-working. In embodiments, to minimize inconsistencies in authentication dynamics as the cold-worked metal articles 20 are subject to surface wear, a surface of the composite coating 14 may be cleared of luminescent phosphor particles 18 prior to cold-working, which may result in more consistent content of luminescent phosphor particles 18 throughout the composite coating 14 after cold-working.

Figure 3:
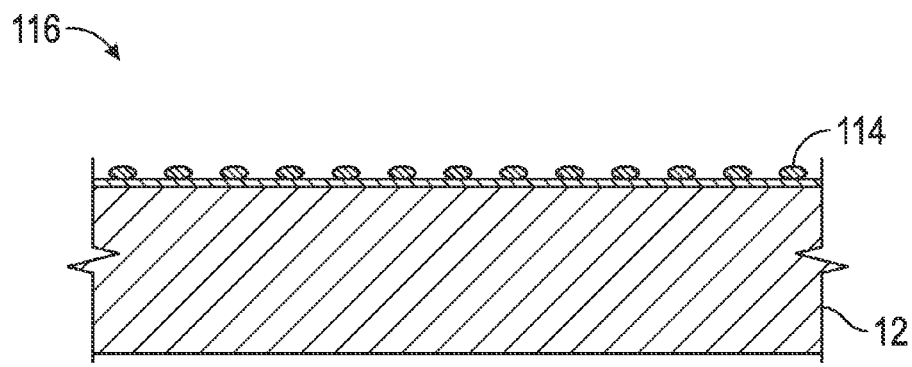
FIG. 3 is a schematic cross-sectional side view of an intermediate article including a metal substrate and a luminescent coating formed thereon that includes luminescent phosphor particles prior to cold-working in accordance with another embodiment.
Figure 4A:
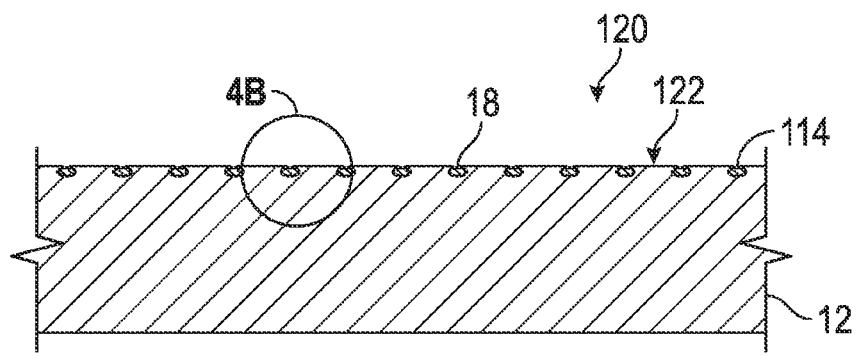
FIG. 4A is a schematic cross-sectional side view of a cold-worked metal article formed from the intermediate article of FIG. 3 after cold-working.
Figure 4B:
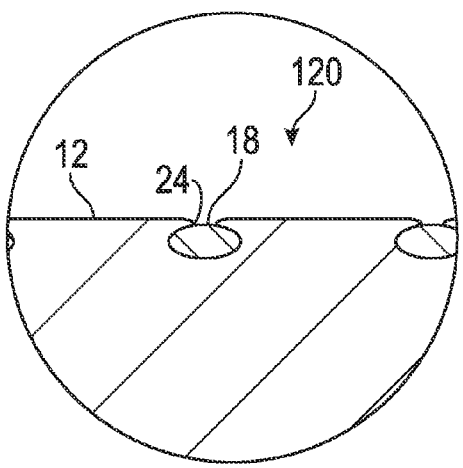
FIG. 4B is a magnified view of a portion of the cold-worked metal article of FIG. 4A.

Another embodiment of a cold-worked metal article and a method of forming the cold-worked metal article will now be described with reference to FIGS. 3 and 4. In this embodiment and as shown in FIG. 3, a metal substrate 12 is provided in the same manner described above. However, in this embodiment, instead of forming the composite coating over the metal substrate 12, a luminescent coating 114 that includes the luminescent phosphor particles 18 is formed on the metal substrate 12 to thereby form an intermediate article 116. The luminescent coating 114 may include only the luminescent phosphor particles 18, or may include additional components such as a binder. Suitable binders include any material that can adhere the luminescent phosphor particles 18 onto the surface of the metal substrate 12 on a temporary or permanent basis prior to cold-working. In this manner, controlled amounts of the luminescent phosphor particles 18 may be provided on the surface of the metal substrate 12 prior to cold-working. The intermediate article 116 is then cold-worked in the same manner as described above. Referring to FIGS. 4A and 4B, a cold-worked metal article 120 is formed having a metal-containing surface 122 that includes pores 24. However, in this embodiment, the metal-containing surface 122 is a surface of the metal substrate 12. Excess binder may be cleaned from the metal-containing surface 122 or remain disposed thereon.

Because the luminescent coating 114 does not include the metal-containing material, greater relative amounts of the luminescent phosphor particles 18 may be present in the luminescent coating 114 than are present in the composite coating described above. Further, the luminescent coating 114 may include fewer particles of larger diameter than are contained in the composite coating described above, and the larger particles may result in larger openings in the pores 24. Generally, larger openings of the pores 24 correlate to more efficient detection. This embodiment is particularly suitable under circumstances where the resulting cold-worked metal article 120 is not subject to significant wear because the luminescent phosphor particles 18 are generally only present near the cold-worked metal-containing surface 122 of the resulting cold-worked metal article 120, e.g., within 1-2 microns of the cold-worked metal-containing surface 122. As such, once the cold-worked metal article 120 is subject to wear, authentication using the luminescent phosphor particles 18 may no longer be possible.

In various embodiments and as alluded to above, the cold-worked metal articles 20, 120 may be value articles or other articles that are desirably authenticated. For example, in embodiments, the cold-worked metal articles 20, 120 are chosen from the group of coins, tokens, casino chips, or medallions. In specific embodiments, the cold-formed metal articles 20 described in the embodiment of FIGS. 1 and 2 may be suitable for coins in circulation. Further, the cold-formed metal articles 20 described in the embodiment of FIGS. 1 and 2 that contain the luminescent phosphor particles 18 that emit at less than or equal to about 1100 nm may be suitable for gaming tokens, coins in circulation, or other articles that may be subject to repeated use in amusement or concession devices. The cold-formed metal articles 120 described in the embodiment of FIGS. 3 and 4 may be suitable for commemorative coins or coins that include high-value materials (such as silver, gold, or platinum coins). In other embodiments, the cold-worked metal articles 20, 120 may be original articles of manufacture that are desirably authenticated as real upon purchase.

To authenticate the cold-worked metal articles 20, 120, the cold-worked metal articles 20, 120 are exposed to light that is produced by an exciting light source. The produced light has sufficient intensity to excite the luminescent phosphor particles 18. Therefore, an appropriate light source may be chosen depending upon the luminescent phosphor particles 18 that are to be detected. The presence of the luminescent phosphor particles 18 in the cold-worked metal articles 20, 120 is then detected with a detector. Various detectors are known in the art for detecting emissions from luminescent phosphor particles 18. For example, silicon detectors are generally employed to detect emissions of less than or equal to about 1100 nm, and other types of detectors are employed that are capable of detecting emissions at greater than about 1100 nm as an alternative or in addition to the silicon detects, depending upon the type of luminescent material that is employed. However, in other embodiments, it is to be appreciated that other types of detectors that are capable of detecting emissions within a band of interest may be used, including detectors that are capable of detecting emissions within the infrared spectrum. Examples of such other types of detectors include lead-sulfide, lead-selenide, germanium, indium-antimonide, indium-arsenide, indium-gallium-arsenide, platinum-silicide, and indium-antimonide detectors.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention. It being understood that various changes may be made in the function and arrangement of elements described in an exemplary embodiment without departing from the scope of the invention as set forth in the appended claims.

What is claimed is:

1. A cold-worked metal article comprising:
   a cold-worked metal-containing surface comprising pores; and
   luminescent phosphor particles disposed within the pores;
   wherein the luminescent phosphor particles comprise:
      a host crystal lattice material; and
      at least one active ion comprising an absorbing ion and an emitting ion different from the absorbing ion;
   wherein the luminescent phosphor particles are harder than the cold-worked metal-containing surface.

2. The cold-worked metal article of claim 1, wherein the host crystal lattice material comprises an oxide-containing material.

3. The cold-worked metal article of claim 2, wherein the oxide-containing material is chosen from an aluminate, a borate, a gallate, a niobate, vanadate, a garnet, a pervoskite, an oxysulfide, and combinations thereof.

4. The cold-worked metal article of claim 1, wherein the absorbing ion is chosen from chromium, iron, erbium, neodymium, ytterbium, and combinations thereof.

5. The cold-worked metal article of claim 4, wherein the absorbing ion is the chromium and wherein the chromium is substituted in the host crystal lattice material in an amount of at least about 1 atomic percent, based on a total number of ions of the host crystal lattice material that may be theoretically substituted.

6. The cold-worked metal article of claim 1, wherein the emitting ion is chosen from erbium, thulium, ytterbium, holmium, neodymium, and combinations thereof.

7. The cold-worked metal article of claim 1, wherein the luminescent phosphor particles emit radiation at a wavelength of less than or equal to about 1100 nm.

8. The cold-worked metal article of claim 7, wherein the host crystal lattice material is a garnet and wherein the absorbing ion comprises chromium.

9. The cold-worked metal article of claim 8, wherein the emitting ion is a first emitting ion having an emission at a wavelength of less than or equal to about 1100 nm, and wherein the at least one active ion further comprises a second emitting ion having an emission at a wavelength of greater than about 1100 nm.

10. The cold-worked metal article of claim 9, wherein the first emitting ion is chosen from ytterbium, neodymium, and combinations thereof, and wherein the second emitting ion is chosen from erbium, thulium, holmium, and combinations thereof.

11. The cold-worked metal article of claim 8, wherein the garnet host crystal lattice material is chosen from yttrium aluminum garnet, yttrium gallium garnet, gadolinium gallium garnet, gadolinium scandium gallium garnet, and mixtures thereof.

12. The cold-worked metal article of claim 1, comprising a metal substrate and a composite coating disposed thereon, wherein the composite coating comprises a metal-containing material with the luminescent phosphor particles dispersed therein and wherein the cold-worked metal-containing surface is further defined as a surface of the composite coating.

13. The cold-worked metal article of claim 12, wherein the luminescent phosphor particles have an average nominal particle diameter of less than or equal to about 2 microns.

14. The cold-worked metal article of claim 1, comprising a metal substrate and a luminescent coating comprising the luminescent phosphor particles disposed thereon, wherein the cold-worked metal-containing surface is further defined as a surface of the metal substrate.

15. The cold-worked metal article of claim 14, wherein the luminescent coating further comprises a binder for adhering the luminescent phosphor particles onto the surface of the metal substrate prior to cold-working.

16. The cold-worked metal article of claim 1, chosen from the group of coins, tokens, casino chips, or medallions.

17. A method of forming a cold-worked metal article, wherein the method comprises the steps of:
   providing a metal substrate having a surface;
   forming a coating on a surface of the metal substrate to produce an intermediate article, wherein the coating comprises luminescent phosphor particles and wherein the luminescent phosphor particles comprise:
      a host crystal lattice material; and
      at least one active ion comprising an absorbing ion and an emitting ion different from the absorbing ion; and
   cold-working the intermediate article to produce the cold-worked metal article.

18. The method of claim 17, wherein forming the coating on the surface of the metal substrate comprises forming a composite coating on the metal substrate, wherein the composite coating comprises a metal-containing material with the luminescent phosphor particles dispersed therein.

19. The method of claim 18, wherein forming the coating on the surface of the metal substrate comprises applying a luminescent coating comprising the luminescent phosphor particles and a binder on the metal substrate.

20. A method of authenticating a cold-worked metal article, wherein the method comprises the steps of:
- providing the cold-worked metal article comprising:
  - a cold-worked metal-containing surface defining pores; and
  - luminescent phosphor particles disposed within the pores;
  - wherein the luminescent phosphor particles comprise:
    - a host crystal lattice material; and
    - at least one active ion comprising an absorbing ion and an emitting ion different from the absorbing ion;
  - wherein the luminescent phosphor particles are harder than the cold-worked metal-containing surface;
- exposing the cold-worked metal article to light produced by an exciting light source that produces the light having sufficient intensity to excite the luminescent phosphor particles; and
- detecting the presence of the luminescent phosphor particles in the cold-worked metal article with a detector.

\* \* \* \* \*